United States Patent [19]

Bullis et al.

[11] 4,049,989
[45] Sept. 20, 1977

[54] ION PRODUCTION MEANS

[75] Inventors: Robert H. Bullis; Walter J. Wiegand, Jr., Glastonbury, both of Conn.

[73] Assignee: United Technologies Corporation, Hartford, Conn.

[21] Appl. No.: 605,562

[22] Filed: Aug. 18, 1975

[51] Int. Cl.² ............................................ H01J 27/00
[52] U.S. Cl. ................................ 313/230; 213/231; 73/194 F
[58] Field of Search ............... 313/230, 231, 231.4, 313/231.5, 359, 360, 361, 363, 364; 315/111, 111.1, 111.2, 111.3, 111.4, 111.8, 111.9; 73/194 R, 194 F

[56] References Cited

U.S. PATENT DOCUMENTS

| | | | |
|---|---|---|---|
| 2,772,364 | 11/1956 | Washburn | 313/230 |
| 2,798,181 | 7/1957 | Foster, Jr. | 313/161 |
| 2,861,452 | 11/1958 | Morgan | 73/194 F |
| 3,258,964 | 7/1966 | Zessoules | 73/194 F |
| 3,470,741 | 10/1969 | Durbin | 73/194 |
| 3,648,517 | 3/1972 | Dorman | 73/194 F |
| 3,835,705 | 9/1974 | Hadjidjanian | 73/194 F |

OTHER PUBLICATIONS

Hollow Cathode Discharge Ion Source by Ko and Winnard, IBM Tech. Discl. Bull. vol. 17, No. 5, Oct., 1974, p. 1379.

*Primary Examiner*—Rudolph V. Rolinec
*Assistant Examiner*—Vincent J. Sunderdick
*Attorney, Agent, or Firm*—Anthony J. Criso

[57] ABSTRACT

Apparatus for providing ions having a specific electric charge to a stream of working fluid are disclosed. The ions are produced by a variety of techniques in a volume of the working fluid which is maintained in a protected region within the stream. An electric field draws ions away from the production region and makes them available to the stream of fluid. In many applications an independent electric field is applied to the flowing fluid to move the ions within the working fluid.

12 Claims, 1 Drawing Figure

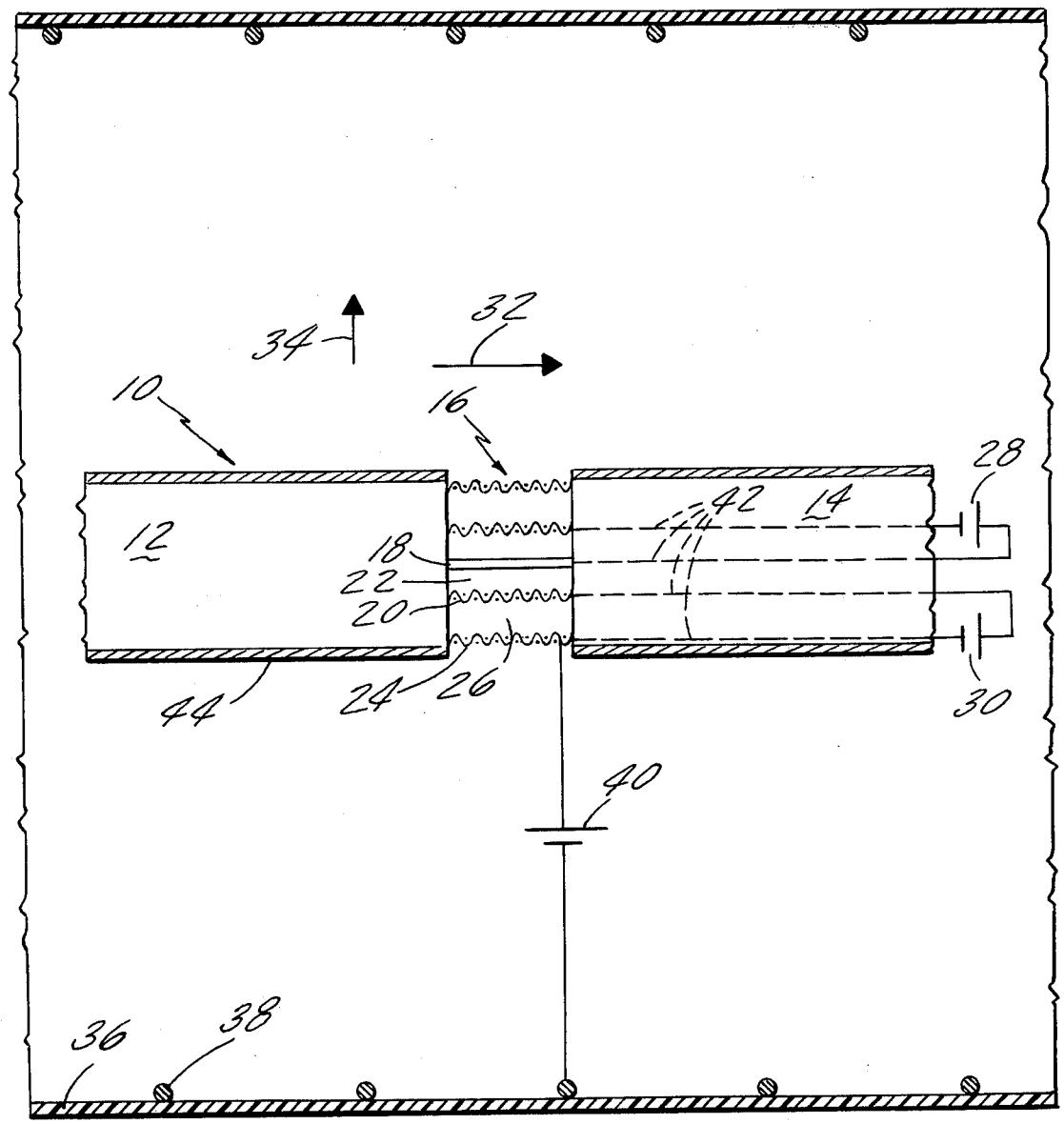

ION PRODUCTION MEANS

BACKGROUND OF THE INVENTION

1. Field of the Invention

The present invention relates to means for providing ions in a fluid and more particularly to means for producing a substantially uniform source of ions having an electric charge of the same sign.

2. Description of the Prior Art

Ions have been found to be very useful in sensing various parameters such as the flux, velocity, or mass flow of a fluid. A typical example of one such application is described in the patent to G. L. Mellen, U.S. Pat. No. 2,637,208 entitled Velocity Measuring By The Use Of High Energy Electrons. Mellen teaches the formation of an ion cloud at a known location and detecting the arrival of such ions at a second location. Means such as a spark gap or ionizing radiation provide the ion cloud required for the measurement. A generally similar teaching is provided by B. Boyd et al in U.S. Pat. No. 2,827,786 entitled Ion Tracer Airspeed Indicator. Boyd et al time the passage of an ion cloud between two known locations and disclose several possible methods of producing the required ionization such as alpha particles, high speed electrons, ultraviolet rays, x-rays and the spectrum of available electric discharges although the art does not dwell on the relative merits of each of such sources.

In U.S. Pat. No. 3,470,741 entitled Mass Flow Meter Apparatus, E. J. Durbin describes a mass flow apparatus having a line source ionization means which is either linear or in the form of a circular disc. Durbin discloses a corona discharge as the means for providing ions although other ion sources are suggested and equally applicable. One of the principal shortcomings of the ionization producing means shown is the sensitivity to particulate matter passing through the device. Foreign particulate matter such as dust or dirt which may be entrained in the fluid entering the system can settle on the emitting electrode causing a nonuniformity in the distribution of emission from the electrode. Similarly, foreign material suspended in the fluid stream itself especially in the areas directly adjacent to the emitting electrode can lead to erratic ion current behavior due to perturbations in the charge distribution in this region. A power supply including means for maintaining a constant ratio of voltage to current between the emitting and collecting electrodes of ion deflection devices is taught in U.S. Pat. No. 3,648,517 entitled Control Apparatus For Mass Flow Meter issued to F. D. Dorman. Although the control for the power supply as disclosed has certain advantages, the basic mass flow meter apparatus disclosed is essentially the same as devices shown in the prior art. A simple and reliable source of ions which is insensitive to the presence of such foreign matter would enhance the practicableness of many devices such as the instruments briefly discussed above.

SUMMARY OF THE INVENTION

An object of the present invention is to provide an ion source having a substantially uniform ion density distribution which represents a major improvement.

According to the present invention a reliable source of ions especially suited for use in sensing parameters of a fluid flowing through a conduit comprises a housing means having an axis extending in the direction of fluid flow and including means for providing ions in a confined volume which is defined axially by the housing means and in the direction perpendicular to the axis by an ion permeable screen, an ion permeable grid adjacent to the screen and means for supplying an electric field between the screen and the grid.

The ions are frequently produced by an electric discharge such as a glow or corona discharge and provide either a straight or circular line source of ions. The apparatus includes an ion permeable electrode and an ion permeable accelerating grid which injects the desired ions into the working area. In many fluid meter applications in which the electric current due to ion migration across the fluid is measured, a migration inducing electric field is applied to the ions. The overall length in the axial direction of the ion producing mechanism is usually small with respect to many of the surrounding components.

An ion source in accordance with the present invention is both rugged and reliable. These devices can be used with any means of initially producing ions and their operations is relatively insensitive to dirt and foreign matter and the environmental fluid. Those embodiments having an electric discharge to produce the ions initially, can have this field optimized independently of the electric field used to draw the ions away from the production region. In some application still another electric field is used to induce migration of the ions in the flowing fluid.

The foregoing and other objects, features and advantages of the present invention will become more apparent in the light of the following detailed description of the preferred embodiment thereof as discussed and illustrated in the accompanying drawing.

BRIEF DESCRIPTION OF THE DRAWING

The FIGURE is a schematic cross sectional view of an ion source in accordance with the present invention.

DESCRIPTION OF A PREFERRED EMBODIMENT

An apparatus for providing ions in accordance with the present invention is shown in the FIGURE. A main assembly 10 having a circular cross section is comprised of an upstream section 12 and a downstream section 14 which are separated from each other by a center region 16. In the center region a center electrode 18 mounted on the centerline of the main assembly 10 and a permeable electrode 20 placed symmetrically about the centerline form an annular electric discharge region 22 therebetween. A grid 24 placed symmetrically about the permeable electrode forms an ion acceleration region 26 between the screen and the grid. An ion power source 28 provides an electric potential between the center and permeable electrodes and an ion acceleration power source 30 provides an electric potential between the permeable electrode and the grid.

The grid 24 is typically a wire mesh having openings at least large enough to allow throughflow of fluid media including gases such as air which in the FIGURE are shown with a flow direction 32. Similarly, the electrode 20 has openings or pores sufficiently large to allow such media to pass therethrough. Thus, when air for example is passed over the main assembly 10 in the direction 32 some of this air enters the acceleration region 26 as well as the discharge region 22. The ion power source 28 maintains an electric potential between the center electrode and the permeable electrode 20 sufficient to ionize the air in the discharge region and produce a continuous supply of ions. The grid is maintained at suitable electrical potential by the power source 30 to extract some of those ions produced in the discharge region which migrate through the porous electrode 20 and accelerate them in a radial direction 34 through the grid 24 which is also ion permeable. These ions are deposited in the stream of the working medium passing over the main assembly.

The main assembly 10 is shown in the FIGURE located in the center of a circular conduit 36 as is often the case in many fluid measurement applications which require the insertion of ions into the fluid as it passes through the conduit. An ion collector 38 shown as a coil of electrically conductive material is located on the inner wall of the conduit and an ion migration power source 40 provides an electric field across the conduit. Various other ion collection means such as conductive coatings can be substituted on the conduit depending upon the particular application.

Both the upstream and downstream sections of the main assembly are made of electrical insulator material having a sufficient dielectric strength to avoid shorting between conductors 42 which connect the power sources to the working elements in the center region. A thin layer 44 of electrically conductive material is applied to the surface of the main assembly exposed to the flow medium to maintain the proper radial electric field configuration through elimination of localized electrical surface charge concentrations which could influence the movement of ions through the main flow.

The present invention is described above in terms of an apparatus having a generally circular cross sectional profile. Such apparatus provides a circular source of ions and in turn an electric current which is essentially evenly injected into a gas passing through a circular pipe having the ion producing means on the centerline. Alternatively, the apparatus can be arranged to provide a line source or a planar source of ions simply by forming the center electrode, the permeable electrode and the grid in an appropriate configuration.

The apparatus as shown functions well with either a glow discharge or a corona discharge between the center electrode and the permeable electrode. Also the electric discharge can be produced with direct current, alternating current or radio frequency power. Further, the ionization in the discharge region can be provided by nonelectrical means such as radioactive sources.

The relative insensitivity of the present invention to dust particles in the working fluid is explained easily with reference to a corona type discharge. The presence of dust or like particles on an electrode which is producing ions has an adverse effect on the uniformity of the ion production and the stability of the resulting current flow. The dust becomes a local site of high emission which can be as large as one to two orders of magnitude greater than the average emission from a comparable clean surface. Also these local perturbations can initiate a pulsating form of corona with resulting ion currents which contain a relatively high level of irregular and uncontrollable noise. In the apparatus shown in the FIGURE, the ion producing or center electrode 18 is located out of the main stream where it is less likely to collect foreign matter that is entrained in the working fluid passing over the main assembly. Perhaps more importantly, the nonuniformity of ion production associated with any dust which may be locally present on the center electrode is significantly reduced by the nature of the plasma processes occurring in the annular electric discharge region as a consequence of the construction and resulting mode of operation of this invention. More specifically, if dust does upset the stability of the ion production around the center electrode 18, the current fluctuations or spatial nonuniformities are averaged out by the plasma and ion permeable electrode 20.

Although the present invention has been shown and described with respect to a preferred embodiment thereof, it should be understood by those skilled in the art that various changes and omissions in the form and detail thereof may be made therein without departing from the spirit and scope of the invention.

Having thus described a typical embodiment of our invention, that which we claim as new and desire to secure by Letters Patent of the United States is:

1. Apparatus for providing ions having a specific electrical polarity to a fluid flowing in a conduit along a flow axis wherein the ions migrate across the fluid in a direction essentially perpendicular to the flow axis and the apparatus comprises:
    a main assembly having an outer surface extending along the axis and including,
        an upstream section,
        a downstream section, and
        a center region which separates the upstream and downstream sections;
    means for producing ions in the center region;
    an ion permeable grid which extends in the axial direction across the center region between the upstream and downstream sections, the grid and the ion producing means defining therebetween an ion acceleration region which is bounded axially at the upstream end by the upstream section and at the downstream end by the downstream section; and
    means for applying a first electric field across the ion acceleration region between the ion production means and the ion permeable grid.

2. The invention according to claim 1 including further ion collection means spaced apart from the ion permeable grid and extending along the axis of the conduit.

3. The invention according to claim 2 including further means for applying a second electric field across the fluid between the ion permeable grid and the ion collection means.

4. The invention according to claim 3 wherein the upstream and downstream sections are formed of a dielectric material covered by a sheath of conductive material.

5. The invention according to claim 4 wherein the main assembly is essentially circular in cross section and both the ion production means and the ion permeable grid are concentric about the centerline of the main assembly.

6. Apparatus for providing ions having a specific electrical polarity to a fluid flowing in a conduit along a flow axis wherein the ions migrate across the fluid in a direction essentially perpendicular to the flow axis and the apparatus comprises:
    a main assembly having an outer surface extending along the axis and including,
        an upstream section,
        a downstream section, and
        a center region which separates the upstream and downstream sections;
    means for producing ions in the center region comprising, an anode, a cathode, and means for applying an ion production electric field between the anode and cathode;

an ion permeable grid which extends in the axial direction across the center regions between the upstream and downstream sections, the grid and the ion producing means defining therebetween an ion acceleration region which is bounded axially at the upstream end by the upstream section and at the downstream end by the downstream section; and means for applying an ion accelerating electric field across the ion acceleration region between the ion production means and the ion permeable grid.

7. The invention according to claim 6 wherein the cathode is an ion permeable member.

8. The invention according to claim 7 wherein the means for applying the electric field between the anode and the cathode can provide an electric field strength sufficient to support a plasma discharge in the center region.

9. The invention according to claim 7 wherein the means for applying the electric field between the anode and the cathode can provide an electric field strength sufficient to support a glow discharge in the center region.

10. The invention according to claim 7 wherein the conduit is formed from a dielectric material.

11. The invention according to claim 10 wherein the cross section profile of the conduit is circular.

12. The invention according to claim 11 wherein the length of the center region along the axis of flow is small with respect to the distance of separation between the main assembly and the conduit.

* * * * *